United States Patent [19]

Drahnak

[11] Patent Number: 4,510,094

[45] Date of Patent: Apr. 9, 1985

[54] PLATINUM COMPLEX

[75] Inventor: Timothy J. Drahnak, St. Paul, Minn.

[73] Assignee: Minnesota Mining and Manufacturing Company, St. Paul, Minn.

[21] Appl. No.: 558,617

[22] Filed: Dec. 6, 1983

[51] Int. Cl.³ .............................................. C07F 17/02
[52] U.S. Cl. .......................... 260/429 CY; 204/159.13; 556/470
[58] Field of Search .................................. 260/429 CY

[56] References Cited

U.S. PATENT DOCUMENTS

| | | | |
|---|---|---|---|
| 2,868,751 | 1/1959 | Johnson et al. | 260/429 CY |
| 3,159,662 | 12/1964 | Ashby . | |
| 3,178,464 | 4/1965 | Pierpoint . | |
| 3,220,972 | 11/1965 | Lamoreaux . | |
| 3,313,773 | 4/1967 | Lamoreaux . | |
| 3,321,501 | 5/1967 | Wilkus et al. | 260/439 CY X |
| 3,326,952 | 6/1967 | Wilkus et al. | 260/429 CY |
| 3,410,886 | 11/1968 | Joy . | |
| 3,470,225 | 9/1969 | Knorre et al. . | |
| 3,567,755 | 3/1971 | Seyfried et al. . | |
| 3,649,660 | 3/1972 | Brown | 260/429 CY |
| 3,814,731 | 6/1974 | Nitzsche et al. . | |
| 4,134,906 | 1/1979 | Oswald et al. | 260/429 CY |
| 4,276,252 | 6/1981 | Kreis et al. | 264/222 |
| 4,288,345 | 9/1981 | Ashby et al. | 252/431 R |
| 4,332,654 | 6/1982 | Yates | 204/158 R |

OTHER PUBLICATIONS

Chemical Abstracts, 75, 129943n, (1971).
Robert A. Faltynek, "Transition–Metal Photocatalysis: Rhodium(i)–Promoted Hydrosilation Reactions", *Inorg. Chem.*, 1981, 20(5), pp. 1357–1362.
S. D. Robinson and B. L. Shaw, *J. Chem. Soc.*, 1965, 1529.

*Primary Examiner*—Helen M. S. Sneed
*Attorney, Agent, or Firm*—Donald M. Sell; James A. Smith; David L. Weinstein

[57] ABSTRACT

A process for the addition of compounds containing silicon-bonded hydrogen to compounds containing aliphatic unsaturation. The process is activated by actinic radiation and is conducted in the presence of a platinum complex having one cyclopentadienyl group that is eta-bonded to the platinum atom and three aliphatic groups that are sigma-bonded to the platinum atom.

2 Claims, No Drawings

PLATINUM COMPLEX

This invention relates to a hydrosilation process involving the reaction of a compound containing silicon-bonded hydrogen with a compound containing aliphatic unsaturation in the presence of actinic radiation, and to compositions which contain an actinic radiation-sensitive catalyst that are useful in said process. The invention further relates to polysiloxane compositions, prepared by said process, which compositions are useful for preparing release-coated substrates.

Numerous patents teach the use of various complexes of cobalt, rhodium, or platinum as catalysts for accelerating the thermally-activated addition reaction (hydrosilation) between a compound containing silicon-bonded hydrogen and a compound containing aliphatic unsaturation. For example, U.S. Pat. No. 4,288,345 (Ashby, et al) discloses as a catalyst for hydrosilation reactions a platinum-siloxane complex. U.S. Pat. No. 3,470,225 (Knorre, et al) discloses production of organic silicon compounds by addition of silicon to organic compounds containing at least one non-aromatic double or triple carbon-to-carbon bond using a platinum compound of the empirical formula $PtX_2(RCOCR'COR'')_2$ wherein X is halogen, R is alkyl, R' is hydrogen or alkyl, and R'' is alkyl or alkoxy. The catalysts disclosed in the foregoing patents are characterized by their high catalytic activity. Other platinum complexes for accelerating the aforementioned thermally-activated addition reaction include: a platinum-cyclopropane complex having the formula $(PtCl_2—C_3H_6)_2$ (U.S. Pat. No. 3,159,662, Ashby); a complex of a platinous salt and an olefin (U.S. Pat. No. 3,178,464, Pierpoint); a platinum-containing complex prepared by reacting chloroplatinic acid with an alochol, ether, aldehyde, or mixtures thereof (U.S. Pat. No. 3,220,972, Lamoreaux); a platinum compound selected from trimethylplatinum iodide and hexamethyldiplatinum (U.S. Pat. No. 3,313,773, Lamoreaux); a hydrocarbyl or halohydrocarbyl nitrile-platinum (II) halide complex (U.S. Pat. No. 3,410,886, by Joy); a hexamethyl-dipyridine-diplatinum iodide (U.S. Pat. No. 3,567,755, Seyfried, et al); a platinum curing catalyst obtained from the reaction of chloroplatinic acid and a ketone having up to 15 carbon atoms (U.S. Pat. No. 3,814,731, Nitzsche, et al); and a platinum compound having the general formula $(R')PtX_2$ where R' is a cyclic hydrocarbon radical or substituted cyclic hydrocarbon radical having two aliphatic carbon-carbon double bonds, and X is a halogen atom or alkyl radical (U.S. Pat. No. 4,276,252, Kreis, et al). Although these platinum complexes and many others are useful as catalysts in processes for accelerating the thermally-activated addition reaction between the compounds containing silicon-bonded hydrogen and compounds containing aliphatic unsaturation, processes for accelerating the ultraviolet radiation activated addition reaction between these compounds are rare. U.S. Pat. No. 4,332,654 (Yates) discloses a process for contacting an organic carbonyl compound with an organosilicon hydride in the presence of a transition metal carbonyl coordination compound and then irradiating the mixture to form a silyl ether. Complexes of platinum are not included among useful catalysts for that process. Faltynek, "Inorganic Chemistry", 20(5), 1357–1362, (1981), discloses that rhodium complexes are active photocatalyst precursors for the hydrosilation reaction. However, rhodium complexes exhibit much lower catalytic activity than do platinum complexes.

In one aspect, this invention is an improved process for the actinic radiation-activated addition reaction of a compound containing silicon-bonded hydrogen with a compound containing aliphatic unsaturation, said addition being referred to as hydrosilation, the improvement comprising using, as a platinum hydrosilation catalyst, an ($\eta$-cyclopentadienyl)tri($\sigma$-aliphatic)platinum complex. The process is applicable both to the synthesis of low molecular weight compounds and to the curing of high molecular weight compounds, i.e. polymers, containing unsaturated groups, e.g.,

For example, the process comprises exposing to actinic radiation, e.g. ultraviolet radiation, a composition capable of undergoing hydrosilation comprising (a)

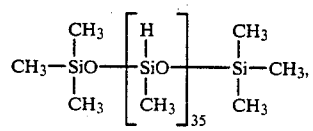

I (b)

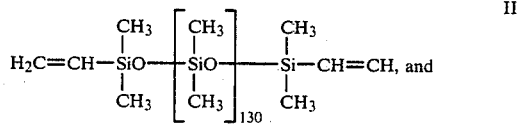

II (c) a platinum complex catalyst having one cyclopentadienyl group that is eta-bonded to the platinum atom and three aliphatic groups that are sigma-bonded to the platinum atom.

The invention further involves novel compositions, capable of undergoing hydrosilation, containing the aforementioned platinum complex.

An important application of the process and compositions of the invention is the in situ curing of polymeric silicone composition to a solid surface to provide a non-stick or low surface energy character to the surface.

Advantages of the platinum complex in accelerating the radiation-activated addition reaction of compounds containing silicon-bonded hydrogen with compounds containing aliphatic unsaturation include:

(1) the reaction composition will not react prematurely or readily in the absence of actinic radiation;
(2) since heat is not required, the addition reaction can be carried out on the surface of a heat-sensitive substrate without adversely affecting the substrate; and
(3) radiation curing consumes less energy than does thermal curing.

As used in this application, the term "compound", unless indicated otherwise, is a chemical substance which has a particular molecular identity or is made of a mixture of such substances, e.g. polymeric substances. The term "hydrosilation" means the addition of organosilicon compounds containing silicon-bonded hydrogen to a compound containing an aliphatic multiple bond, and in the hydrosilation process described in this application, it refers to those processes in which platinum-containing catalysts are used to effect the addition of an organosilicon compound having a silicon-bonded hydrogen atom to an aliphatically unsaturated compound having either olefinic or acetylenic unsaturation.

In a preferred embodiment of the invention, the platinum complex is an (η-cyclopentadienyl)tri(σ-aliphatic)-platinum complex having the formula

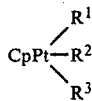   III wherein
Cp represents cyclopentadienyl group that is eta-bonded to the platinum atom, the cyclopentadienyl group being unsubstituted or substituted by one or more groups that do not interfere in a hydrosilation reaction, and
each of $R^1$, $R^2$, and $R^3$ represents an aliphatic, preferably saturated, group having from one to eighteen carbon atoms, said $R^1$, $R^2$, and $R^3$ groups being sigma-bonded to the platinum atom.

The groups represented by $R^1$, $R^2$, and $R^3$ can be unsubstituted or substituted hydrocarbyl groups, or unsubstituted or substituted acyl groups, said substituents, if any, not interfering in a hydrosilation reaction. The groups can be straight-chain, branched-chain, and, if sufficiently large, cyclic.

The ($\eta^5$-cyclopentadienyl)trimethylplatinum complexes can be prepared by the addition of a solution of cyclopentadienylsodium in tetrahydrofuran to an equimolar amount of trimethylplatinum iodide dissolved in benzene, and isolation of the product complex from the filtrate, according to the procedure of S. D. Robinson and B. L. Shaw, J. Chem. Soc. 1965, 1529. Other ($\eta^5$-cyclopentadienyl)-trialiphaticplatinum complexes can be prepared by using corresponding amounts of substituted cyclopentadienylsodium in place of cyclopentadienylsodium and various trialiphatic platinum halides in place of trimethylplatinum iodide.

In an especially preferred embodiment of the invention, the platinum complex is a novel compound within the limits of Formula III, in which the cyclopentadienyl group has as substituents one or more organosilyl groups. The novel complexes exhibit greater solubility and stability in polysiloxane-containing compositions and provide higher gelling rates when irradiated with ultraviolet light than do corresponding complexes not having the organosilyl substitution. The more preferred complex has the formula

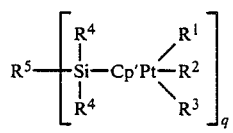   IV wherein
$R^1$, $R^2$, and $R^3$ are as defined for Formula III;
Cp' represents a cyclopentadienyl group that is eta-bonded to the platinum atom and is also bonded to the silicon atom of an organosilyl group;
each $R^4$ can be the same or different and represents a monovalent hydrocarbyl group selected from the group consisting of saturated linear aliphatic groups having 1 to 18 carbon atoms, saturated branched aliphatic groups having 3 to 18 carbon atoms, alicyclic groups having 4 to 18 carbon atoms, aryl groups having 6 to 14 carbon atoms, and

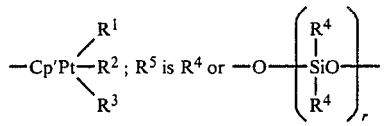

where r is zero or an integer of 1 to 100; and q is one or two, with the proviso that when q is one, $R^5$ is $R^4$, and when q is two, $R^5$ is

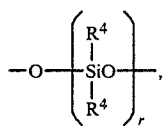

and that in the complex no more than one-half of the $R^4$ groups are

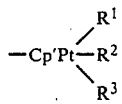

groups.

Representative examples of suitable ($\eta^5$-cyclopentadienyl)trialiphaticplatinum complexes useful in the practice of this invention include the following, in which (Cp) is intended to mean ($\eta^5$-cyclopentadienyl) group:
(Cp)trimethylplatinum
(Cp)ethyldimethylplatinum
(Cp)diethylmethylplatinum
(Cp)triethylplatinum
(Cp)triisopropylplatinum
(Cp)triethylplatinum
(Cp)tri(2-butyl)platinum
(Cp)triallylplatinum
(Cp)tripentylplatinum
(Cp)trihexylplatinum
(Cp)trinonylplatinum
(Cp)tridodecylplatinum
(Cp)tricyclopentylplatinum
(Cp)tricyclohexylplatinum
(methyl-Cp)trimethylplatinum
(chloro-Cp)trimethylplatinum
(fluoro-Cp)trimethylplatinum
(Cp)dimethylbenzylplatinum
(trimethylsilyl-Cp)trimethylplatinum
(triethylsilyl-Cp)trimethylplatinum
(dimethylphenylsilyl-Cp)trimethylplatinum
(methyldiphenylsilyl-Cp)trimethylplatinum
(triphenylsilyl-Cp)trihexylplatinum
[1,3-bis(trimethylsilyl)-Cp]trimethylplatinum
(dimethyloctadecylsilyl-Cp)trimethylplatinum
1,3-bis[(Cp)trimethylplatinum]tetramethyldisiloxane
1,3-bis[(Cp)trimethylplatinum]dimethyldiphenyldisiloxane 1,3-bis[(Cp)dimethylphenylplatinum]tetramethyldisiloxane
1,3,5-tris[(Cp)trimethylplatinum]pentamethyltrisiloxane
1,3,5,7-tetra[(Cp)trimethylplatinum]heptamethyltetrasiloxane
(methoxy-Cp)trimethylplatinum
(ethoxymethyl-Cp)ethyldimethylplatinum
(methyoxycarbonyl-Cp)trimethylplatinum
(1,3-dimethyl-Cp)trimethylplatinum
(methyl-Cp)triisopropylplatinum
(1,3-diacetyl-Cp)diethylmethylplatinum
(1,2,3,4,5-pentachloro-Cp)trimethylplatinum
(phenyl-Cp)trimethylplatinum
(Cp)acetyldimethylplatinum
(Cp)propionyldimethylplatinum
(Cp)acryloyldimethylplatinum
(Cp)di(methacryloyl)ethylplatinum
(Cp)dodecanoyldimethylplatinum
trimethylplatinumcyclopentadienyl-terminated polysiloxane having random units of

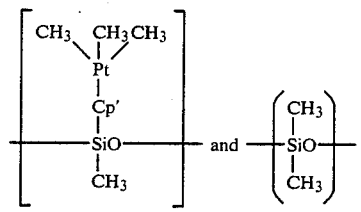

where Cp′ represents the cyclopentadienyl group.

Turning now to the reactants to be used in the radiation-activated addition reaction, compounds containing aliphatic unsaturation which are useful in the present invention have olefinic or acetylenic unsaturation. These compounds are well-known in the art of hydrosilation and are disclosed in such patents as U.S. Pat. No. 3,159,662 (Ashby); U.S. Pat. No. 3,220,972 (Lamoreaux); and U.S. Pat. No. 3,410,886 (Joy), which disclosures of said compounds are incorporated herein. In instances where these compounds contain elements other than carbon and hydrogen, it is preferred that these elements be either oxygen, nitrogen, silicon, a halogen, or mixtures of these other elements. The aliphatically unsaturated compound can contain one or more carbon-to-carbon multiple bonds. Representative examples of the aliphatically unsaturated hydrocarbons which can be employed include mono-olefins, for example, ethylene, propylene, and 2-pentene, diolefins, for example, divinylbenzene and butadiene, cycloolefins, for example, cyclohexene and cycloheptene, and monoalkynes, for example, acetylene, propyne, and 1-butene-3-yne. The aliphatically unsaturated compounds can have up to 20 to 30 carbon atoms, or more.

Oxygen-containing aliphatically unsaturated compounds can also be used, especially where the unsaturation is ethylenic, such as methylvinyl ether, divinylether, phenylvinyl ether, monoallyl ether of ethylene glycol, allyl aldehyde, methylvinyl ketone, phenylvinyl ketone, acrylic acid, methacrylic acid, vinylacetic acid, vinyl acetate, and linolenic acid. Heterocyclic compounds containing aliphatic unsaturation in the ring, such as dihydrofuran, and dihydropyrene, are also suitable for the present invention.

Halogenated derivatives of the previously mentioned aliphatically unsaturated compounds can be employed, including the acyl chlorides as well as compounds containing a halogen substituent on a carbon atom other than a carbonyl carbon atom. Such halogen-containing compounds include, for example, vinyl chloride, and the vinylchlorophenyl esters.

Unsaturated compounds containing nitrogen substituents such as acrylonitrile, N-vinylpyrrolidone alkyl cyanide, nitroethylene, etc., are also useful in the practice of the present invention.

Other unsaturated compounds useful in the practice of the present invention include polymers containing aliphatic unsaturation, such as the polyester resins prepared from polybasic saturated or unsaturated acids with polyhydric unsaturated alcohols, and the polyester resins prepared by reacting unsaturated polybasic acids with saturated polyhydric alcohols.

A particularly useful type of unsaturated compound which can be employed in the practice of the present invention is that containing silicon, such as those compounds commonly referred to as organosilicon monomers or polymers. These unsaturated organosilicon compounds have at least one aliphatically unsaturated organic radical attached to silicon per molecule. The aliphatically unsaturated organosilicon compounds include silanes, polysilanes, siloxanes, silazanes, as well as monomeric or polymeric materials containing silicon atoms joined together by methylene or polymethylene groups or by phenylene groups.

Preferred among the aliphatically unsaturated organosilicon compounds useful in the present invention are the monomeric silanes having the empirical formula $$R_b^6R_c^7SiX_{(4-b-c)} \qquad \text{V}$$

the cyclopolysiloxanes having the empirical formula $$(R^6R^7SiO)_d \qquad \text{VI}$$

and the polyorganosiloxanes having the empirical formula $$R_e^6R_f^7SiO_{(4-e-f)/2} \qquad \text{VII}$$

wherein
$R^6$ represents a monovalent aliphatic unsaturated hydrocarbyl group,
$R^7$ represents a monovalent saturated hydrocarbyl group,
X represents a hydrolyzable group,
b is an integer from 1 to 4, inclusive,
c is zero or an integer from 1 to 3, inclusive, the sum of b and c being 1 to 4,
d is an integer from 3 to 18, inclusive,
e is a number having a value of 0.0001 to 1, inclusive, and
f is zero or a number such that the sum of e and f is equal to 1 to 2, inclusive.

Monovalent aliphatic unsaturated hydrocarbyl groups represented by $R^6$ include alkenyl, for example, vinyl, propenyl, isopropenyl, 3-butenyl, and 5-hexenyl. Groups represented by $R^7$ include, for example, alkyl groups, such as methyl, ethyl, and pentyl; cycloalkyl groups, such as cyclopentyl and cyclohexyl; aryl groups such as phenyl and tolyl; aralkyl groups, such as benzyl and phenylethyl; halogenated hydrocarbyl groups, such as haloalkyl, e.g., chloromethyl, trichloromethyl, and 3,3,3-trifluoropropyl, and haloaryl, e.g., chlorophenyl. Hydrolyzable groups represented by X include, for example, halogen groups such as chloro, bromo, and iodo, alkoxy groups such as methoxy, ethoxy, and phenoxy, and acyloxy groups such as acetoxy, propionoxy, and benzoyloxy. A hydrolyzable group is one which undergoes a displacement reaction with water.

In one particularly preferred embodiment of the process of the invention, the compound containing aliphatic unsaturation is an aliphatically unsaturated polyorganosiloxane represented by the general formula:

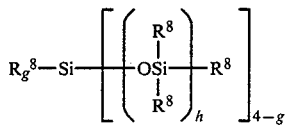

wherein
each $R^8$ can be the same or different and represents an unhalogenated or halogenated ethylenically-unsaturated group having from 2 to 12 carbon atoms, such as the vinyl, propenyl, and chlorovinyl, an unhalogenated or halogenated alkyl group having from 1 to 18 carbon atoms, such as the methyl, ethyl, propyl, hexyl, octyl, dodecyl, octadecyl, trichloromethyl, trifluoromethyl, and 3,3,3-trifluoropropyl, an unhalogenated or halogenated cycloalkyl group having from 3 to 12 carbon atoms, such as the cyclopentyl and cyclohexyl, or phenyl group, at least 90% of all $R^8$ groups being methyl groups, but no more than 10% of all $R^8$ groups being vinyl or propenyl, and at least two of the $R^8$ groups being vinyl or propenyl;
h is a number having a value from about 75 to 250 such that the polyorganovinylsiloxane has a viscosity from about 0.3 to 3 pascal-seconds (300 to 3000 centipose) at 25° C.;
g is 0, 1, 2, or 3.

The reactant containing the silicon-hydrogen linkage can be a polymeric compound or a compound that is not polymeric. These compounds are well-known in the art and are disclosed in the patents which described the aliphatically unsaturated reactant, i.e., Ashby, U.S. Pat. No. 3,159,662; Lamoreaux, U.S. Pat. No. 3,220,972; and Joy, U.S. Pat. No. 3,410,886. The reactant containing the silicon-hydrogen linkage should contain at least one silicon-bonded hydrogen atom per molecule, with no more than two hydrogen atoms attached to any one silicon atom.

Some classes of compounds having a silicon-bonded hydrogen atom which can be used in the invention are organosilanes having the empirical formula $(H)_j Si(R^9)_k(X)_{(4-j-k)}$ 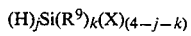 VIII organocyclopolysiloxanes having the empirical formula $(HR^9SiO)_d$  IX and organohydrosiloxane polymers or copolymers having the empirical formula $(R^9)_f Si(H)_e O_{(4-e-f)/2}$ 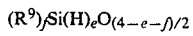 X wherein
$R^9$ represents an organic group, preferably selected from the group consisting of monovalent hydrocarbyl groups, halogenated monovalent hydrocarbyl groups, and cyanoalkyl groups,
j is the integer 1 or 2,
k is zero or an integer of 1 to 3, inclusive, the sum of j and k being equal to 1 to 4,
X, d, e and f are as defined above for formulas IV, V, and VI.

Among the groups represented by $R^9$ include, for example, alkyl groups having 1 to 18 carbon atoms, e.g., methyl, ethyl, propyl, octyl, and octadecyl, cycloalkyl groups having 5 to 7 ring carbon atoms, e.g., cyclohexyl and cycloheptyl, aryl groups having 6 to 18 carbon atoms, e.g., phenyl, naphthyl, tolyl, xylyl, and combinations of alkyl and aryl groups, e.g., aralkyl groups, such as, benzyl and phenylethyl, and halo-substituted groups thereof, e.g., chloromethyl, chlorophenyl, and dibromophenyl. Preferably, the $R^9$ group is methyl or both methyl and phenyl. The $R^9$ group can also be an unsaturated aliphatic group having 1 to 20 carbon atoms, such as alkenyl or cycloalkenyl, e.g., vinyl, allyl and cyclohexenyl. When the $R^9$ group is a group with aliphatic unsaturation, the silicon compound containing silicon-hydrogen linkages can be reacted with itself to form a polymer.

Among the inorganic compounds which contain silicon-bonded hydrogen atoms and which are useful as reactants in the process of the present invention are included, for example, trichlorosilane, dibromosilane, pentachlorodisilane, pentachlorodisiloxane, and heptachlorotrisilane.

A preferred compound having silicon-bonded hydrogen useful in this invention is a polyorganohydrosiloxane having the general formula:

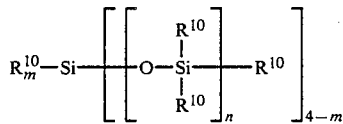

wherein
each $R^{10}$ can be the same or different and represents hydrogen, an alkyl group having 1 to 12 carbon atoms, a cycloalkyl group having 3 to 12 carbon atoms, a phenyl group, a hydroxyalkyl group having 2 to 6 carbon atoms, or a (polyalkoxy)alkyl group having 1 to 3 alkoxy radicals of which each alkyl radical has 1 to 3 carbon atoms, at least two but not more than one-half of all the $R^{10}$ groups in the siloxane being hydrogen;
m is 0, 1, 2, or 3; and
n is a number having an average value from 1 to 275 such that when considered with the value of m provides a molecular weight to the polyorganohydrosiloxane of between 134 and 20,000.

The hydrosilation composition useful in the synthesis of low molecular weight compounds by the process of the invention can be prepared by mixing 0.1 to 10.0 equivalent weights (a) of the compound having silicon-bonded hydrogen with one equivalent weight of (b) the compound having aliphatic unsaturation and then adding an amount of platinum complex catalyst sufficient to catalyze the reaction. The amount of the catalyst can range from 5 to 1000 parts by weight, preferably from 50 to 500 parts by weight, per 1,000,000 parts by weight of the total composition.

Known techniques can be used to conduct the hydrosilation reation. In carrying out a hydrosilation reaction in the practice of this invention, the reactants and catalyst can be introduced into a vessel equipped for stirring, where the mixture is stirred until it is homogenous. If either of the reactants is a solid or is extremely viscous, a solvent can be introduced into the vessel to facilitate uniform mixing of the reactants. Suitable solvents include aromatic hydrocarbons, such as xylene and toluene, aliphatic hydrocarbons, such as hexane and mineral spirits, and halogenated hydrocarbons, such as chlorobenzene and trichloroethane. Where the activating energy for the reaction is to be actinic radiation, it is desirable that the solvent be transmissive to the radiation. From 0.1 to 10 parts of solvent per part by weight of the combined reactants may be used. The resulting reaction product will generally be sufficiently pure for the use to which it is intended. However, it may be desirable to remove the solvent if one has been employed.

The hydrosilation compositions useful in the preparation of higher molecular weight cured siloxane polymers, by the process of this invention, can be prepared by mixing about 60 to about 99 parts by weight of an aliphatically unsaturated polysiloxane and about 1 to about 40 parts by weight of the compound having silicon-bonded hydrogen and then adding from 5 to 1000 parts by weight, preferably from about 50 to about 500 parts by weight of platinum complex catalyst per 1,000,000 parts by weight of the total composition. The actual ratio of compound having silicon-bonded hydrogen to aliphatically unsaturated polysiloxane can be adjusted so that about 0.1 to about 10 SiH groups are provided for each aliphatically unsaturated group, e.g.,

The reaction mixture can be mixed, as by stirring, blending, or tumbling, until it is homogenous.

The thoroughly mixed composition can then be applied to a substrate by any suitable means, such as by spraying, dipping, knife coating, curtain coating, roll coating, or the like, and the coating cured by using conventional irradiation techniques. It is preferred that curing be conducted by exposing the coated substrate to actinic, preferably ultraviolet (UV) radiation. Depending on the particular silicone formulation, catalyst, and intensity of the ultraviolet radiation, curing can be accomplished in a period from less than 30 minutes to less than one second. Shorter curing times are preferred for the reason that greater production levels can be attained. Any radiation source emitting radiation below about 4000 Å can be used. Conventional low, medium, and high pressure mercury lamps are useful radiation sources. Examples of suitable radiation sources include lamps such as the GE H3T and the Hanovia 450 W arc lamp. Radiation sources rich in ultraviolet, such as fluorescent lamps and "black" lights, are also useful. Particularly preferred sources of UV radiation are continuous processors which are capable of continuously exposing webs coated with the composition of the invention at rates up to about 300 meters per minute or more. Such processors are exemplified by the RPC Processor in which the radiation source is provided by medium pressure lamps each emitting about 40–120 watts/cm. With the RPC Processor, curing of coatings of the hydrosilation composition can be accomplished at a rate of about 15 meters/minute. Curing can also be accomplished by heating at a temperature of about 50° C. to 250° C. for 5 minutes to less than about 15 seconds, the higher temperatures requiring shorter times.

The hydrosilation reaction and curing process can be accelerated for some of the platinum complex catalysts, particularly at the longer wavelengths (e.g., wavelengths as emitted by "black" light sources), by including in the composition a soluble compound having an absorption bond at about 3300 to 3900 Å and a triplet energy of about 60 to 70 kcal mole$^{-1}$. Representative of these compounds are thioxanthene-9-one and 2-chlorothioxanthene-9-one.

Various additives conventionally included in hydrosilation compositions can be included in the curable compositions, depending on the intended purpose of the compositions. Fillers and/or pigments, such as chopped fibers, crushed polymers, talc, clay, titanium dioxide, and fumed silica can be added. Soluble dyes, oxidation inhibitors and/or any material that does not interfere with the catalytic activity of the platinum complex and is transparent to ultraviolet radiation at a wavelength below about 4000 Å (if ultraviolet radiation is to be used to bring about the hydrosilation reaction) can be added to the composition.

When it is desired to modify the release character of the cured organosilicone compositions of the invention, that is, increase the adhesive release level from the surface of the cured organosilicone composition from a low value of less than about 10 g/2.5 cm width to a higher value of 20 to 400 g/2.5 cm width or more, conventional release modifiers can be added to the composition. Examples of such release modifiers are graft polymers having a polyorganosiloxane segment and an organic polymer segment, as described in U.S. Pat. No. 4,366,286 (Friemann, et al); vinyl terminated diorganopolysiloxane copolymers, e.g., a vinyl end-blocked diorganopolysiloxane in which from 3 to 39 mole percent of the nonterminal siloxane units are diphenylsiloxane units and at least 50 mole percent of the remaining organic radicals on the siloxane units are methyl radicals as described in U.S. Pat. No. 4,154,714 (Hockemeyer, et al); the three-dimensional toluene-soluble silicate resins, known in the silicate art as MQ resins (for a general discussion of MQ silicone resins, see Chapter One of Noll, Chemistry and Technology of Silicones, 2d ed., 1968) which are the cohydrolysis product of a mixture of one or more hydrolyzable silanes of the formula $(R)_cSiY_{4-c}$ in which R is a monovalent hydrocarbon group attached to silicon, Y is a hydrolyzable group, and c is zero or the integer 1, 2, and 3. Such compounds are known in the art and are described in part in U.S. Pat. No. 3,936,582 (Keiser) and more fully in U.S. Pat. Nos. 2,676,182 (Daudt, et al) and 2,857,356 (Goodwin), which patents are incorporated herein by reference. Another compound of this type is the reaction product of MQ resins with organohydrogenpolysiloxanes as is described in U.S. Pat. Nos. 4,310,678 (Blizzard, et al) and 4,322,518 (Blizzard). A preferred MQ modifier is that obtained by the cohydrolysis of one mole (CH$_3$)$_3$SiCl and one to two moles of Si(OC$_2$H$_5$)$_4$ followed by reaction with [(CH$_3$)$_2$Si]$_2$NH or [(CH$_2$=CH)(CH$_3$)$_2$Si]$_2$NH to reduce the hydroxyl level of the modifier to less than 1.0 percent by weight.

The shelf life of the curable compositions containing the catalyst can be extended by the addition of a conventional catalyst inhibitor. The amount of catalyst inhibitor can vary from about 1 to about 10 times or more the amount of platinum complex, depending on the activity of the particular complex or complex-accelerator used and the self life desired for the composition. Greater amounts of inhibitor should be used with the more active complexes, with lesser amounts being used for the less active complexes. Representative catalyst inhibitors include the acetylenic inhibitors, such as the acetylenic alcohols, particularly 3,5-dimethylhexyn-3-ol, and the olefinic siloxanes, such as polymethylvinylcyclosiloxane having three to six methylvinylsiloxane units per molecule.

The hydrosilation compositions of this invention can be applied to the surface of any solid substrate for a variety of purposes. Examples of such surfaces including those of paper, cardboard, wood, cork, plastic such as polyester, nylon, polycarbonate, etc., woven and nonwoven fabric such as cotton, polyester, nylon, etc., metal, glass, and ceramic. The composition can be applied to the surface and cured thereon to provide a non-stick or low surface energy character to the surface. The composition is particularly suitable for providing a release coating for use in pressure sensitive tapes and sheets, for providing a non-stick surface for packaging sheets, and for providing a coating to containers used for the storage of sticky substances.

It is often advantageous to prime the surface of nonporous substrates to which the hydrosilation composition is to be applied to improve the adhesion of the composition to the substrate. Many primers and priming techniques (e.g., corona treatment) are described in the art and should be chosen on the basis of the substrate to be used. For example, the epoxy-functional siloxanes as taught in U.S. Pat. No. 4,243,718 (Murai, et al) are useful for priming the surface of plastic films such as polyester and polyvinylchloride.

Advantages of this invention are further illustrated by the following examples, where the parts referred to are parts by weight. The particular materials and amounts recited as well as other conditions and details given should not be construed to unduly limit this invention.

EXAMPLE 1

This example illustrates the preparation of (trimethylsilyl cyclopentadienyl)trimethyl platinum. Trimethylsilylcyclopentadiene was prepared according to the procedure of A. Davidson and P. E. Rakita, Inorg. Chem.9 289 (1970). To 240 parts of the unpurified yellow solution was added 30 parts of 1.7M n-butyllithium solution at 0° C. The resulting solution was warmed to room temperature and stirred for one hour. Eighteen parts of this solution were added to a vessel containing 1.1 parts of [IPt(CH$_3$)]$_4$, 11 parts tetrahydrofuran, and 11 parts toluene. The resulting mixture was stirred for 16 hours and then worked up by the addition of an equal volume of water, separation and drying of the organic layer, and removal of volatiles under vacuum. The resulting product was purified by column chromatography, giving a pale yellow oil whose analytical data was consistent with the expected compound.

EXAMPLES 2–10

A stock composition was prepared by mixing in a glass container 97.5 parts by weight of vinyl-terminated polysiloxane having the formula:

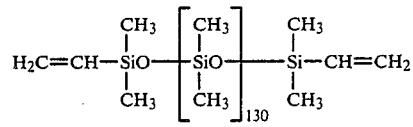

and 2.5 parts by weight of a compound containing silicon-bonded hydrogen group (available as DC 1107 from Dow Corning Corporation) having the formula:

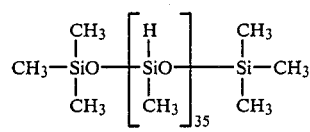

To 50 gram portions of the stock composition was added 15 to 25 milligrams of the ($\eta$-cyclopentadienyl)tri($\sigma$-aliphatic)platinum hydrosilation catalysts listed in Table I, and each portion thoroughly mixed, resulting in compositions containing 200 parts of platinum per million parts of total composition. Five gram sub-portions of each 50 gram portion of the composition were treated as follows:

Sub-portion 1 was sealed in an amber vial, and the time for the composition to react at 23° C. to a state in which it would no longer flow when the vial was turned end over end was measured and recorded in Table I. This time is referred to as the "dark gel time".

Sub-portions 2, 3 and 4 were placed on a "Kofler Heizbank" heat bar and the gel time at 100° C., 150° C. and 200° C., respectively, was measured and recorded in Table I.

Sub-portion 5 was placed in a clear glass jar under ambient laboratory fluorescent lights and the time for the composition to react to a state in which it would no longer flow was measured and recorded in Table I.

Sub-portion 6 was exposed to the radiation from a 20 watt "black" light for 10 seconds then held in the dark. The time for the composition to react to a state in which it would no longer flow (including the irradiation time) was measured and recorded in Table I.

Sub-portion 7 was exposed to radiation from the 20 watt "black" light for 20 seconds and placed in the dark. As for sub-portion 6, the time to react to a state in which the compositions would no longer flow was recorded in Table I.

Sub-portion 8 was exposed to the radiation from the 20 watt "black" light and the time for the composition to gel (no longer flow) under the "black" light was measured and recorded in Table I.

Sub-portion 9 was prepared by diluting 5 parts by weight of a catalyst-containing sub-portion with 195 parts by weight of stock composition to provide a composition to provide a composition containing 5 parts of platinum per million parts of composition. Sub-portion 9 was exposed to the radiation of a 140-watt medium pressure mercury vapor ultraviolet lamp and the time for the composition to gel (no longer flow) was measured and recorded in Table I.

TABLE I

| | Platinum catalyst | Gel Times | | | | | | | | |
|---|---|---|---|---|---|---|---|---|---|---|
| | | Dark | | | | Fluorescent light | Black light | | | Mercury lamp |
| Ex. No. | ($\eta^5$-Cp) tri($\sigma$-aliphatic)platinum | 23° C.[a] (hr) | 100° C.[b] (min) | 150° C.[b] (sec) | 200° C.[b] (sec) | (c) (min) | 10 sec[d] (sec) | 20 sec[e] (sec) | (f) (sec) | (g) (sec) |
| 2 | (Cp)trimethylplatinum | >1550 | 20 | 23 | 3–4 | 135 | 150–180 | 35 | 23 | 7–10 |
| 3 | (Methyl-Cp)trimethylplatinum | 576 | — | 27 | 2–3 | 135 | 90–130 | 40 | 27 | 8–10 |
| 4 | (1,2,3,4,5-Pentamethyl-Cp) trimethylplatinum | 72 | 20 | 25 | 2–3 | 100 | 60–90 | 40 | 40 | 90–105 |
| 5 | (Cp)Dimethylethylplatinum | 480 | — | 33 | 2–3 | 126 | 70–105 | 40 | 26 | 8 |
| 6 | (Cp)Dimethylacetylplatinum | 48 | 2 | 6 | 1–6 | 100 | 300 | 120 | 30–35 | 10–15 |
| 7 | (Trimethylsilyl-Cp)trimethylplatinum | 430 | — | 26 | 2–3 | 100 | 35 | — | 18 | 7 |
| 8 | (Methoxycarbonyl-Cp)trimethylplatinum | 30 | — | 28 | 4–6 | 85 | 60–65 | 30–35 | 23 | 10 |
| 9 | (Dimethylphenylsilyl-Cp) trimethylplatinum | 500 | — | 35 | 4 | 75 | 23–25 | — | 16 | 7 |
| 10 | 1,3-Bis[Cp—trimethylplatinum]-tetramethyldisiloxane | <360 | — | 60 | 5 | 60 | 40 | 29 | 22 | 7 |

[a] Dark gel time of composition containing 200 ppm of platinum at room temperature
[b] Gel time of composition containing 200 ppm of platinum as determined on a Kofler Heizbank heat bar
[c] Gel time of composition containing 200 ppm of platinum in a clear glass jar continuously exposed to fluorescent lights
[d] Gel time of composition containing 200 ppm of platinum exposed to irradiation of 20 watt black light for 10 sec only
[e] Gel time of composition containing 200 ppm of platinum exposed to irradiation of 20 watt black light for 20 sec only
[f] Gel time of composition containing 200 ppm of platinum exposed to irradiation of 20 watt black light
[g] Gel time of composition containing 5 ppm of platinum exposed to irradiation of medium pressure mercury vapor lamp

COMPARATIVE EXAMPLES A–E

The procedure of Examples 1–9 was repeated, the only exception being that platinum catalysts outside the scope of the invention were used. The results are recorded in Table II.

TABLE II

| | | Gel Times | | | | | | | | |
|---|---|---|---|---|---|---|---|---|---|---|
| | | Dark | | | | Fluorescent light | Black light | | | Mercury lamp |
| Ex. | Platinum Catalyst | 23° C.[a] (hr) | 100° C.[b] (sec) | 150° C.[b] (sec) | 200° C.[b] (sec) | (c) (hr) | 10 sec[d] (min) | 20 sec[e] (hr) | (f) (min) | (g) (sec) |
| A | $H_2PtCl_6$ | 4 | — | — | — | — | — | — | >60 | — |
| B | [IPt (methyl)$_3$]$_4$ | 4 | — | 27 | 3–4 | 168 | — | >1.2 | 4.5–5.5 | 120 |
| C | (COD)[h]Pt(ethyl)$_2$ | 1.75 | 12 | 2 | — | 0.75 | 42 | 0.25 | 3–3.5 | — |
| D | (COD)Pt(4-methylphenyl)$_2$ | 24 | 8 | — | — | 8 | — | >3 | 2.5–3 | — |
| E | (COD)Pt(perfluorophenyl)$_2$ | >2200 | 50 | 24 | 2 | >25 | — | >3 | 5.0–5.5 | — |

[a] Dark gel time of composition containing 200 ppm of platinum at room temperature
[b] Gel time of composition containing 200 ppm of platinum as determined on a Kofler Heizbank heat bar
[c] Gel time of composition containing 200 ppm of platinum in a clear glass jar continuously exposed to fluorescent lights
[d] Gel time of composition containing 200 ppm of platinum exposed to irradiation of 20 watt black light for 10 sec only
[e] Gel time of composition containing 200 ppm of platinum exposed to irradiation of 20 watt black light for 20 sec only
[f] Gel time of composition containing 200 ppm of platinum continuously exposed to irradiation of 20 watt black light
[g] Gel time of composition containing 5 ppm of platinum and exposed to irradiation of medium pressure mercury vapor lamp
[h] COD signifies cyclooctadiene The data of Table I show that hydrosilation compositions containing 200 ppm platinum, as contained in catalysts of the present invention, gel under "black" light in 40 seconds or less and are resistant to gelation at room temperature for 48 hours or more. The data of Table II show that hydrosilation compositions containing 200 ppm of platinum, as contained in catalysts of the prior art, do not gel under "black" light for 2.5 minutes or longer, nearly 4 times the "black" light gel time of the compositions of the present invention. The data of Table I also show that by merely irradiating the compositions of the present invention for a brief period only, e.g. 10 sec to 20 sec, and then removing the radiation source, complete gellation can occur within a matter of no more than a few minutes. In contrast, compositions not within the scope of the present invention, when irradiated for a brief period only, require a much longer period for gellation to occur. Thus, it can be seen that the compositions of the present invention provide for more efficient utilization of equipment and space, as well as energy.

EXAMPLES 11–14

Examples 11–14 illustrate the release character of coatings prepared with the composition of this invention.

Polyethylene coated kraft paper was coated at a coating weight of 2 to 6 grams per square meter with the compositions of Examples 1, 2, 4, and 5 and cured by exposure to ultraviolet radiation provided by two medium pressure mercury lamps operating at the lamp power and speed shown in Table III. The release value of each cured silicone coating and the readhesion values of pressure-sensitive tapes that had been pressed onto the release coated papers were determined and recorded in Table III.

The release value of the cured silicone coating was determined by the following procedure:

A heptane-isopropanol solution of pressure-sensitive adhesive comprising 95.5:4.5 isooctyl acrylate:acrylic acid copolymer, as described in Example 5 of U.S. Pat.

No. Re. 24,906, incorporated herein by reference, was applied to the cured silicone coatings at a coating weight of 32 g/m² (dry weight) and dried for 5 minutes at 70° C. in a circulating air oven. Then a 38 micrometer biaxially oriented film of polyethylene terephthalate (PET) was pressed against the surface of the coating producing a laminate consisting of a pressure-sensitive adhesive tape and a silicone-coated substrate. The laminate was cut into 2.5×25 cm strips. The "release value" was the force required to pull the PET film with adhesive adhered thereto (i.e., a pressure-sensitive adhesive tape) away from the silicone-coated substrate at an angle of 180° and a pulling speed of 230 cm/min. The release value recorded in Table III is the average of at least three determinations.

The readhesion values of the pressure-sensitive tapes were determined by the following procedure:

The pressure-sensitive tapes, as removed from the siicone-coated surface, were applied to the surface of a clean glass plate. The readhesion value was measured by pulling the tape from the glass surface at an angle of 180° and a stripping speed of 230 cm/min. The readhesion value recorded in Table III is the average of at least three determinations.

TABLE III

| Ex. No. | Catalyst | Lamp power[a] | Speed (m/min) | Release value[b] | Readhesion value[b] |
|---|---|---|---|---|---|
| 11 | (Cp)trimethylplatinum | 120 | 25 | 5 | 1530 |
| 12 | (Methyl-Cp)trimethylplatinum | 80 | 60 | 5 | 1500 |
| 13 | (Cp)diethylmethylplatinum | 80 | 30 | 5 | 1420 |
| 14 | (Cp)dimethylacetylplatinum | 80 | 15 | 5 | 1445 |

[a] watts per centimeter of lamp length
[b] grams per 2.5 cm of width

A control readhesion value of 1500 grams per 2.5 cm of width for the pressure-sensitive tape was obtained by applying the pressure-sensitive tape, which had not been placed in contact with a silicone-coated surfaces to a clean glass plate and the measuring the force required to remove the tape from the plate. The data in Table III show that hydrosilation compositions containing radiation activatable platinum catalysts are useful for providing release-coated substrates.

EXAMPLE 15-21

The procedure of Examples 11-14 was repeated with the exceptions that in Examples 15-19, compositions of the stock composition containing ($\eta^5$-cyclopentadienyl)trimethyl platinum and in Examples 20-21, compositions of the stock composition containing (dimethylphenylsilylcyclopentadienyl)trimethyl platinum were coated onto various substrates at a coating weight of 1 gram per square meter and cured by one pass under one medium pressure mercury lamp operating with a lamp power of 120 watts per centimeter and a speed of 15 to 30 meters per minute as shown in Table IV.

TABLE IV

| Ex. No | Parts per million platinum | Substrate | Speed (m/min) | Release value (g/2.5 cm) | Readhesion value (g/2.5 cm) |
|---|---|---|---|---|---|
| 15 | 180 | A | 30 | 6-7 | 1500 |
| 16 | 100 | B | 15 | 7-8 | 1500 |
| 17 | 200 | B | 15 | 7-8 | 1530 |
| 18 | 100 | C | 15 | 9-12 | 1445 |
| 19 | 200 | C | 15 | 8-10 | 1560 |
| 20 | 200 | D | 27 | 6 | 1430 |
| 21 | 200 | D | 18 | 6 | 1550 |

A = Polyethylene coated kraft paper
B = Biaxially oriented polypropylene film
C = Super calendered kraft paper
D = Polypropylene film It can be seen from Table IV that hydrosilation compositions containing radiation activated platinum catalysts are useful for providing a release coating on various substrates.

EXAMPLE 22

The procedure of Examples 15-21 was repeated with the exception that to 100 parts of the stock composition were added 25 parts of a silicone release modifier. The silicone release modifier was an MQ resin in which the ratio of M units, i.e., $(CH_3)_3SiO_{\frac{1}{2}}$ to Q units, i.e., $SiO_{4/2}$ was 0.7. It was prepared by the cohydrolysis of one mole of trimethylsilyl chloride and 1.4 moles of tetraethyl silicate as is described in U.S. Pat. No. 2,676,182 (Daudt, et al). The hydroxyl content of the cohydrolysis product was reduced to less than one percent by the reaction of 60 grams of the cohydrolysis product with 3.3 grams of hexamethyl disilizane at 100° C. for 8 hours. To the resulting composition was added 200 ppm of ($\eta^5$-cyclopentadienyl)trimethylplatinum, and the mixed composition was coated onto polyethylene-coated Kraft paper and cured as described in Examples 15-21 at a speed of 15 meters per minute. The release value found for the cured coating was 14 to 15 grams per 2.5 cm of width and readhesion value was 1460 grams per 2.5 cm thus demonstrating that with the radiation activated catalysts, hydrosilation comprising containing a silicone release modifier are useful for providing modified release-coated substrates.

EXAMPLE 23

The procedure of Examples 11-14 was repeated using in place of the vinyl-terminated polydimethylsiloxane a vinyl-terminated polysiloxane having the formula

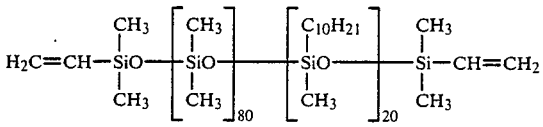

To it was added 200 ppm platinum in the form of ($\eta^5$-cyclopentadienyl)trimethylplatinum and the catalyzed mixture was coated as described in Examples 11-14 and cured at 15 meters/minute. The cured coating had a release value of 23 g/2.5 cm and a readhesion value of 1650 g/2.5 cm. This example demonstrates that polysiloxanes having substituents other than the methyl group can be used in the compositions of this invention.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A platinum complex having the formula

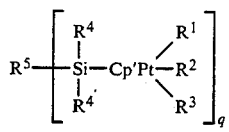

wherein

Cp′ represents a cyclopentadienyl group that is eta-bonded to the platinum atom and is also bonded to the silicon atom of an organosilyl group;

each of $R^1$, $R^2$, and $R^3$ represents an aliphatic group having from one to eighteen carbon atoms, said $R^1$, $R^2$, and $R^3$ groups being sigma-bonded to the platinum atom each $R^4$ can be the same or different and represents a monovalent hydrocarbyl group selected from the group consisting of saturated linear aliphatic groups having 1 to 18 carbon atoms, saturated branched aliphatic groups having 3 to 18 carbon atoms, alicyclic groups having 4 to 18 carbon atoms, aryl groups having 6 to 14 carbon atoms, and

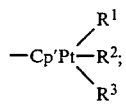

$R^5$ is $R^4$ or

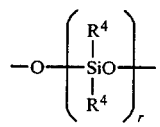

where r is zero or an integer of 1 to 100; and q is one or two, with the proviso that when q is one, $R^5$ is $R^4$, and when q is two, $R^5$ is

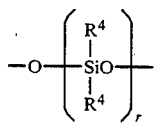

and that in the complex no more than 50% of the $R^4$ groups are

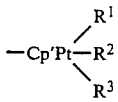

groups.

2. A platinum complex according to claim 1 selected from the group consisting of:
($\eta^5$-trimethylsilylcyclopentadienyl)trimethylplatinum,
($\eta^5$-phenyldimethylsilylcyclopentadienyl)trimethylplatinum,
(1,3-bis[($\eta^5$-cyclopentadienyl)trimethylplatinum]tetramethyldisiloxane,
1,3,5-tris[($\eta^5$-cyclopentadienyl)trimethylplatinum]pentamethyltrisiloxane, and
trimethylplatinumcyclopentadienyl terminated polysiloxane having random units of

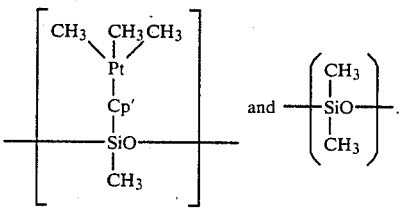

where Cp′ represents the cyclopentadienyl group.

* * * * *

UNITED STATES PATENT AND TRADEMARK OFFICE
CERTIFICATE OF CORRECTION

PATENT NO. : 4,510,094

DATED : April 9, 1985

INVENTOR(S) : Timothy J. Drahnak

It is certified that error appears in the above-identified patent and that said Letters Patent is hereby corrected as shown below:

Col. 11, line 6, "self" should read --shelf--.

Signed and Sealed this

Twenty-fourth Day of September 1985

[SEAL]

Attest:

Attesting Officer

DONALD J. QUIGG

Commissioner of Patents and Trademarks—Designate